(12) United States Patent
Harper et al.

(10) Patent No.: US 7,951,108 B2
(45) Date of Patent: May 31, 2011

(54) DUAL CHAMBER MIXING SYRINGE AND METHOD FOR USE

(75) Inventors: Derek J. Harper, Goleta, CA (US); Charles L. Johnson, Ventura, CA (US); Joseph Kovalski, Ventura, CA (US)

(73) Assignee: MDC Investment Holdings, Inc., Wilmington, DE (US)

( * ) Notice: Subject to any disclaimer, the term of this patent is extended or adjusted under 35 U.S.C. 154(b) by 0 days.

(21) Appl. No.: 12/236,721

(22) Filed: Sep. 24, 2008

(65) Prior Publication Data

US 2009/0018496 A1 Jan. 15, 2009

Related U.S. Application Data

(63) Continuation of application No. 10/972,985, filed on Oct. 25, 2004, now abandoned.

(60) Provisional application No. 60/514,045, filed on Oct. 24, 2003.

(51) Int. Cl.
*A61M 37/00* (2006.01)
*A61M 5/00* (2006.01)

(52) U.S. Cl. .............. 604/82; 604/87; 604/89; 604/248; 604/191

(58) Field of Classification Search .............. 604/82–92, 604/248, 191
See application file for complete search history.

(56) References Cited

U.S. PATENT DOCUMENTS

| | | | |
|---|---|---|---|
| 877,946 A | 2/1908 | Overton | |
| 2,869,543 A | 1/1959 | Ratcliff et al. | |
| 3,326,215 A | 6/1967 | Sarnoff et al. | |
| 3,477,432 A | 11/1969 | Denman | |
| 3,489,147 A * | 1/1970 | Shaw | 604/88 |
| 3,563,373 A | 2/1971 | Paulson | |
| 3,570,486 A * | 3/1971 | Engelsher et al. | 604/88 |
| 3,636,950 A | 1/1972 | Gomez et al. | |
| 3,677,245 A | 7/1972 | Welch | |
| 3,724,460 A | 4/1973 | Gomez et al. | |
| 3,735,761 A | 5/1973 | Hurschman et al. | |
| 3,754,644 A | 8/1973 | Hampel | |
| 3,785,379 A | 1/1974 | Cohen | |
| 3,838,689 A | 10/1974 | Cohen | |
| 4,040,420 A | 8/1977 | Speer | |
| 4,059,109 A * | 11/1977 | Tischlinger | 604/88 |
| 4,171,698 A | 10/1979 | Genese | |
| 4,188,949 A | 2/1980 | Antoshkiw | |
| 4,405,317 A | 9/1983 | Case | |
| 4,581,016 A | 4/1986 | Gettig | |
| 4,755,169 A | 7/1988 | Sarnoff et al. | |
| 4,861,335 A | 8/1989 | Reynolds | |
| 4,936,315 A | 6/1990 | Lineback | |
| 5,032,117 A | 7/1991 | Motta | |
| 5,067,948 A | 11/1991 | Haber et al. | |
| 5,281,198 A | 1/1994 | Haber et al. | |
| 5,566,729 A | 10/1996 | Grabenkort et al. | |
| 5,569,193 A | 10/1996 | Hofstetter et al. | |
| 5,779,668 A | 7/1998 | Grabenkort | |
| 5,876,372 A | 3/1999 | Grabenkort et al. | |
| 6,217,556 B1 * | 4/2001 | Ellingson et al. | 604/167.01 |

* cited by examiner

*Primary Examiner* — Nicholas D Lucchesi
*Assistant Examiner* — Rebecca E Eisenberg
(74) *Attorney, Agent, or Firm* — Rutan & Tucker, LLP

(57) ABSTRACT

A mixing syringe and method for using the mixing syringe are provided. The mixing syringe comprises a housing having a first compartment for containing a first component, an outer plunger having a second compartment for containing a second component, and an inner plunger. Prior to use, a seal separates the first and second components. To prepare the mixture, the seal is pierced and the two components are mixed. The mixing syringe and its method of use are particularly suited to applications in which at least one of the mixture components is a relatively highly viscous material.

22 Claims, 13 Drawing Sheets

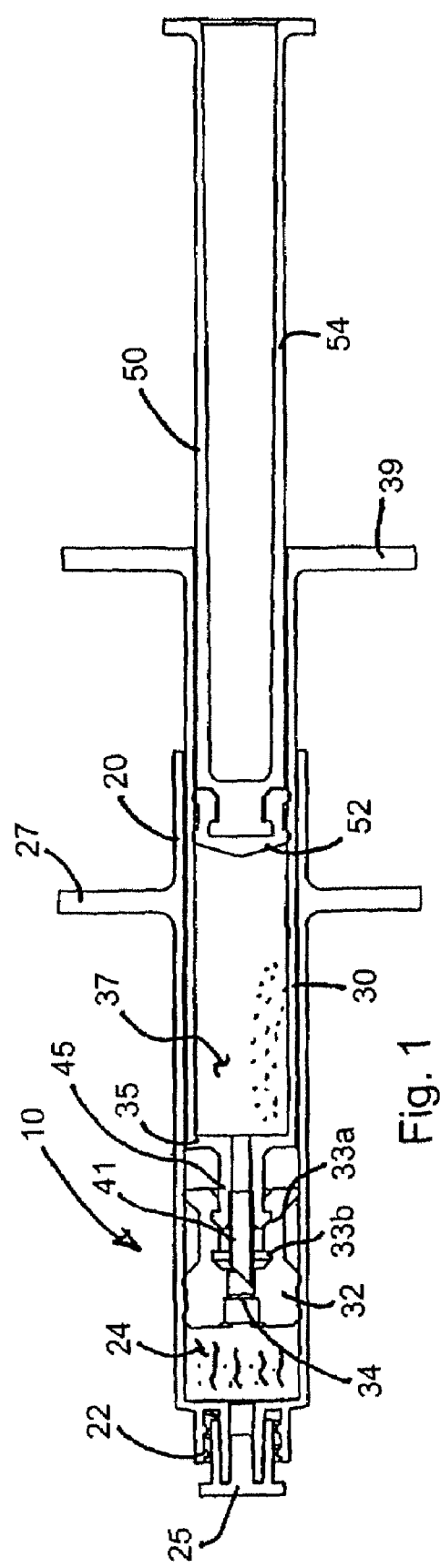
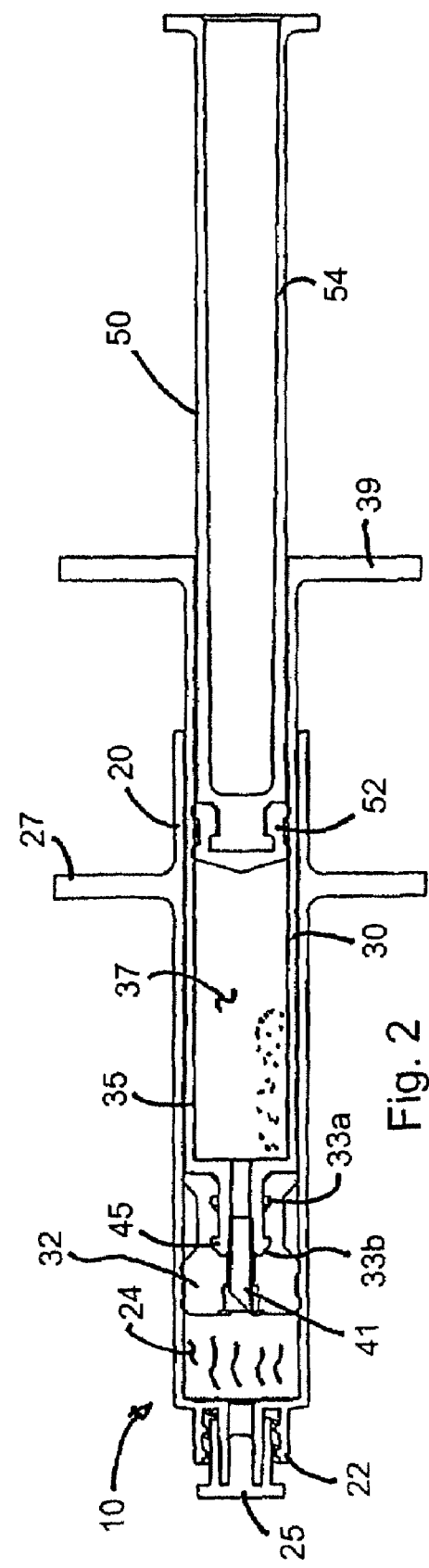

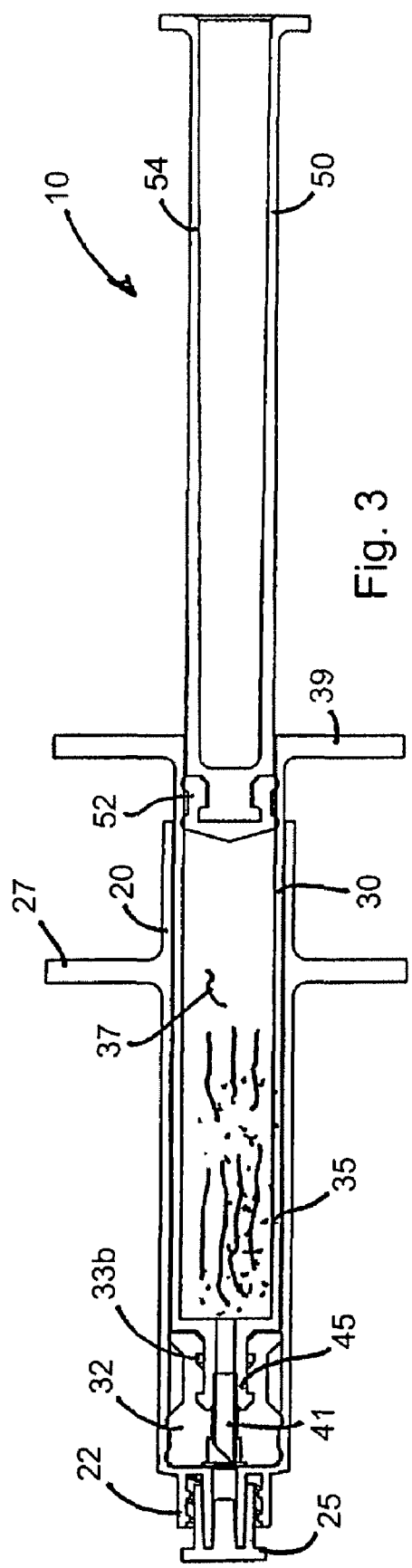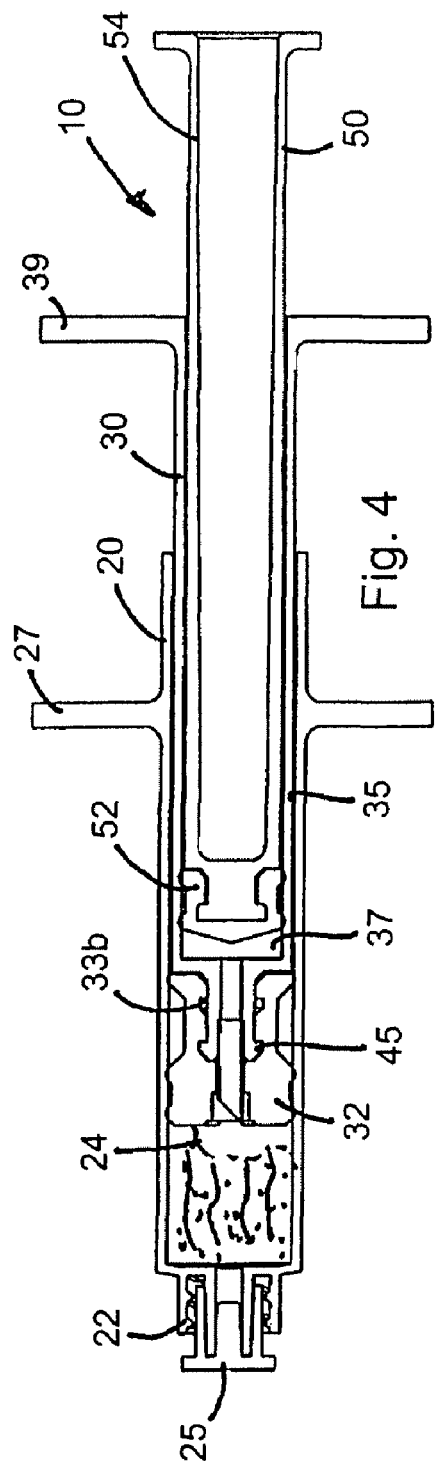

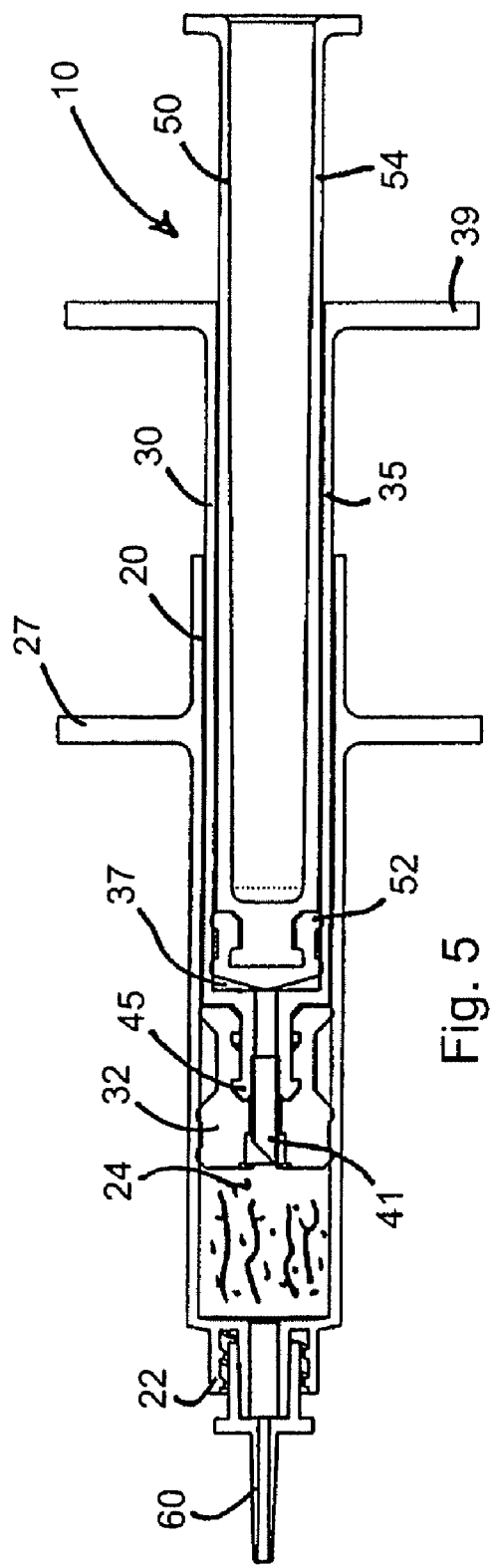
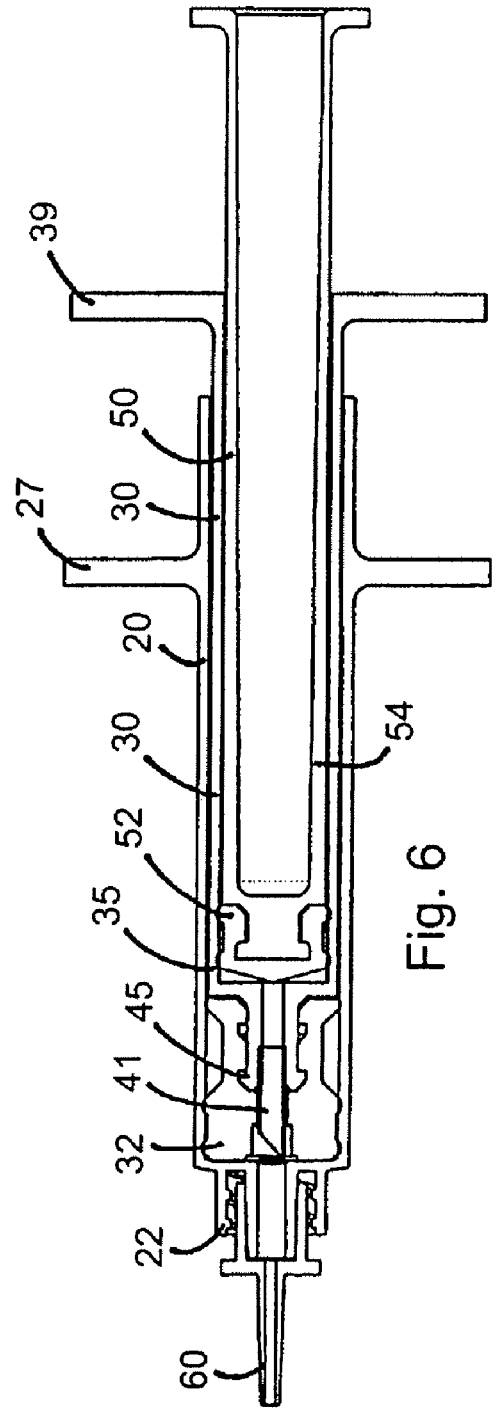
Fig. 5
Fig. 6

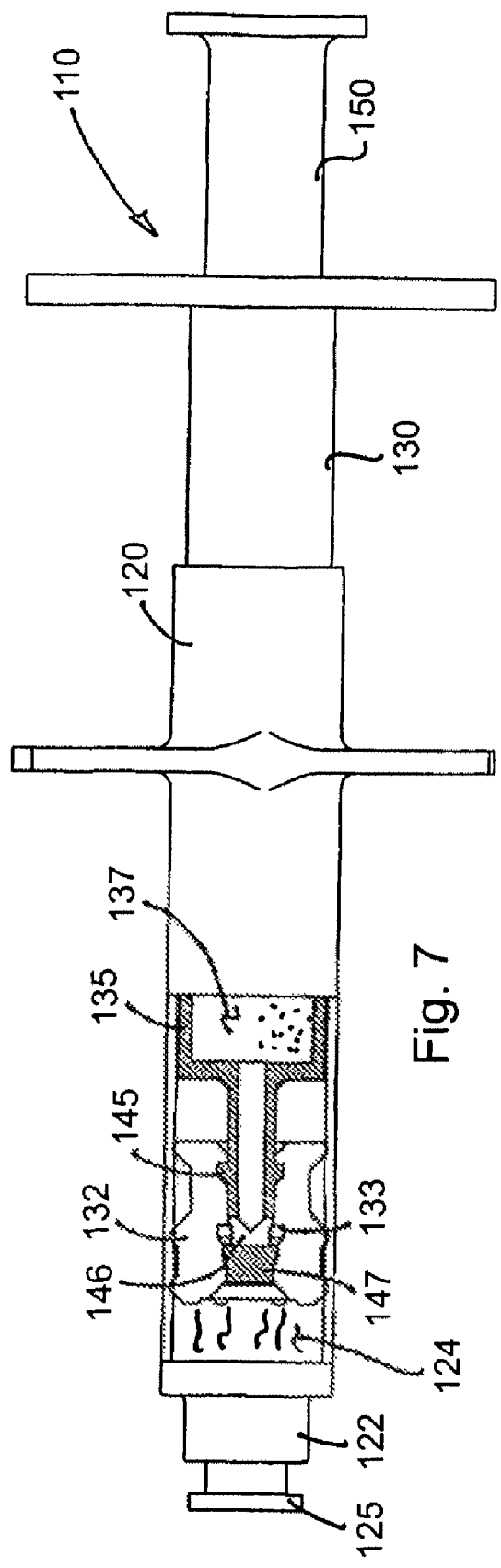
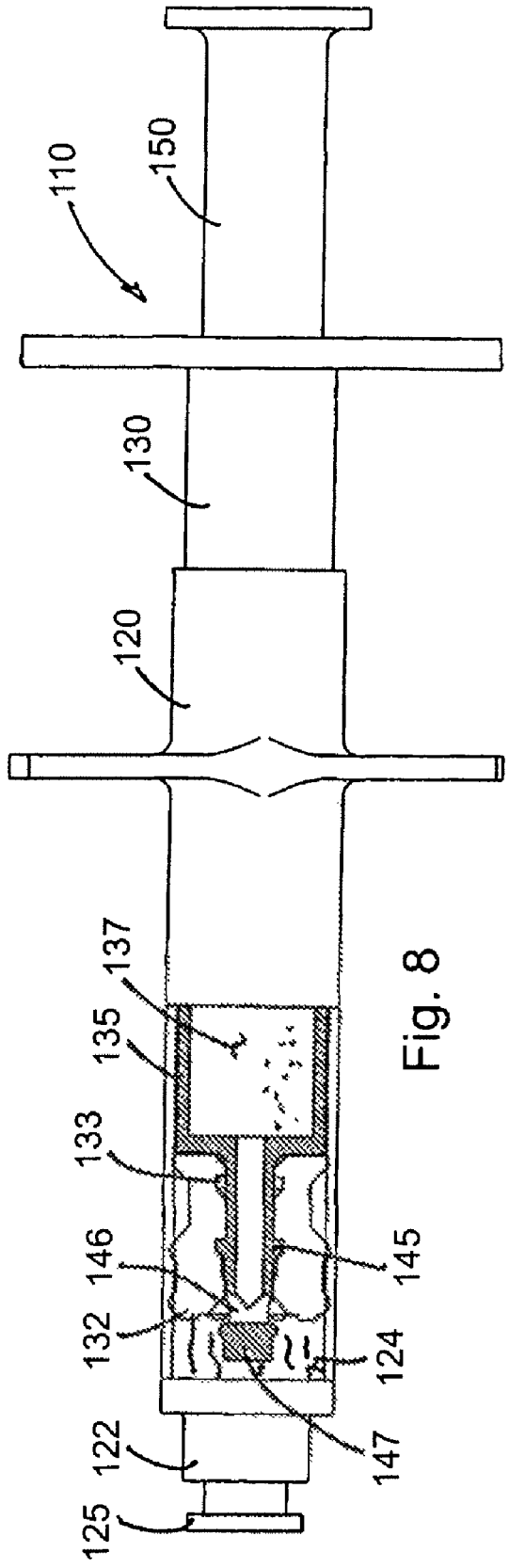
Fig. 7
Fig. 8

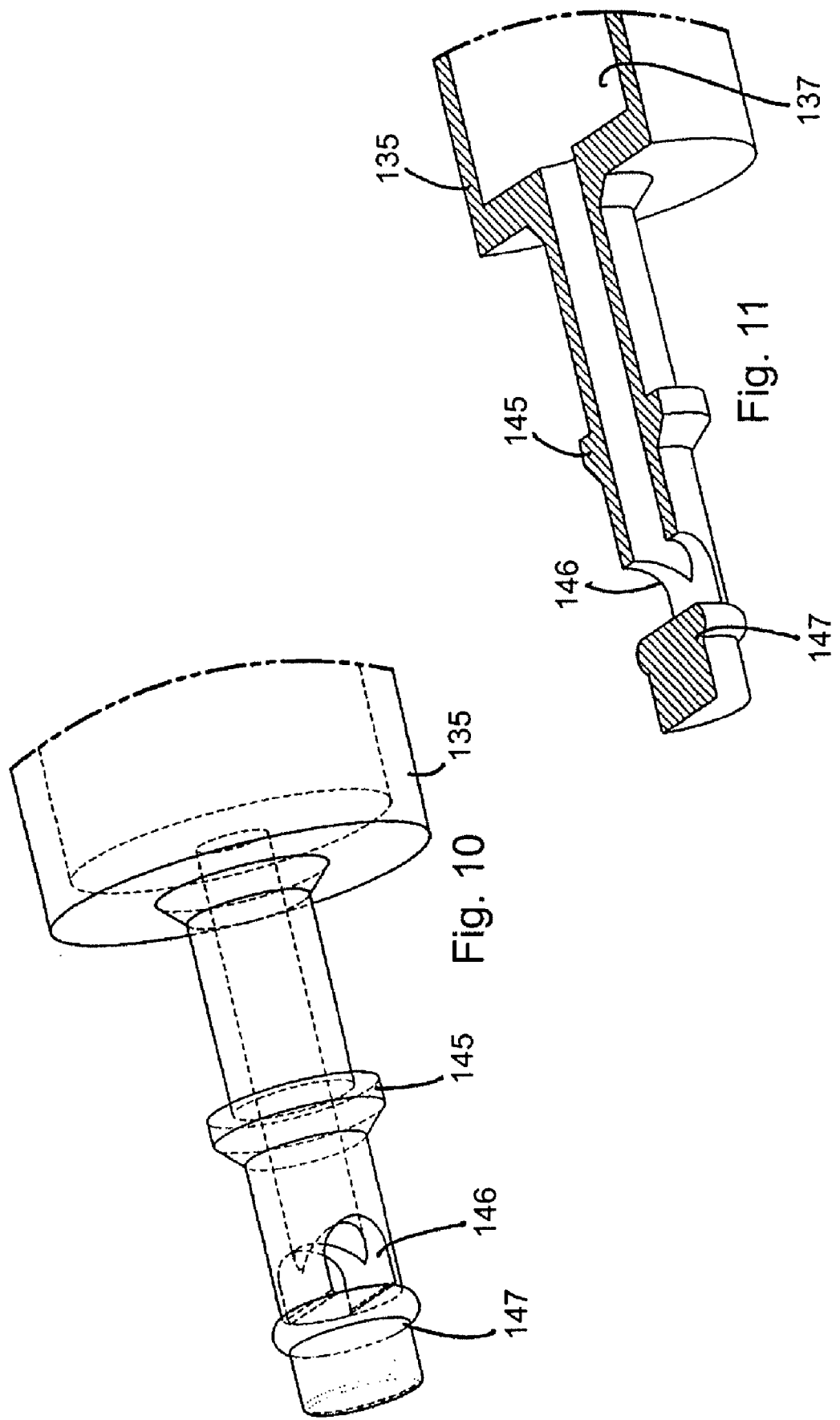

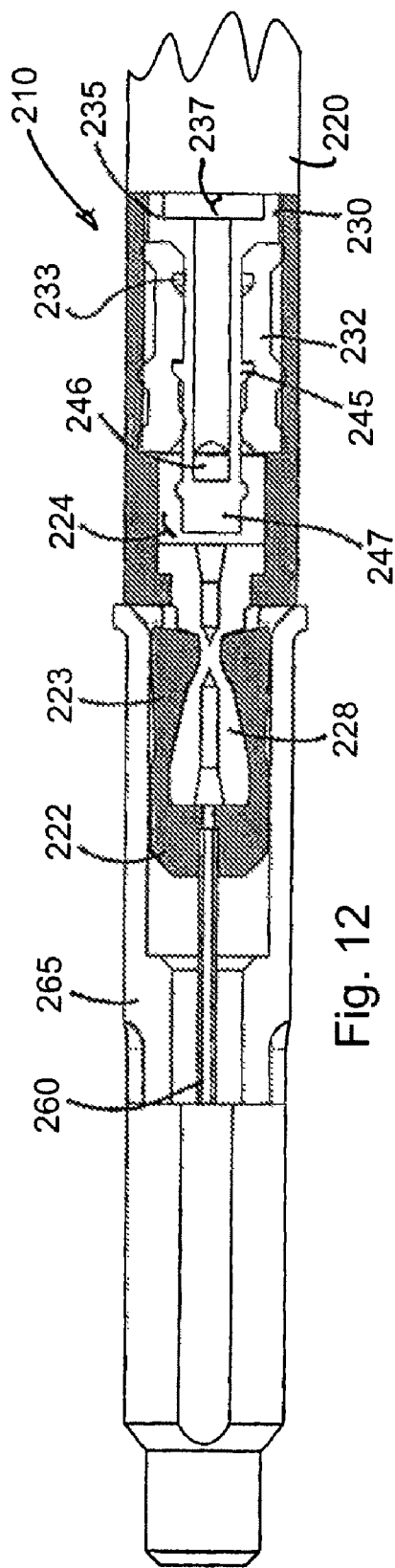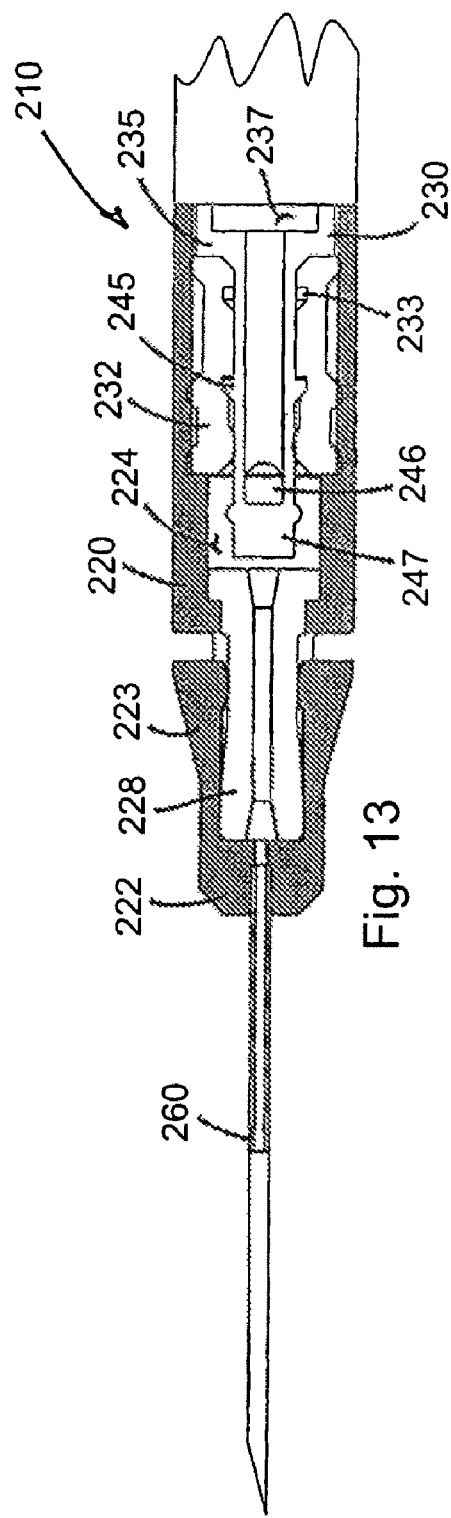

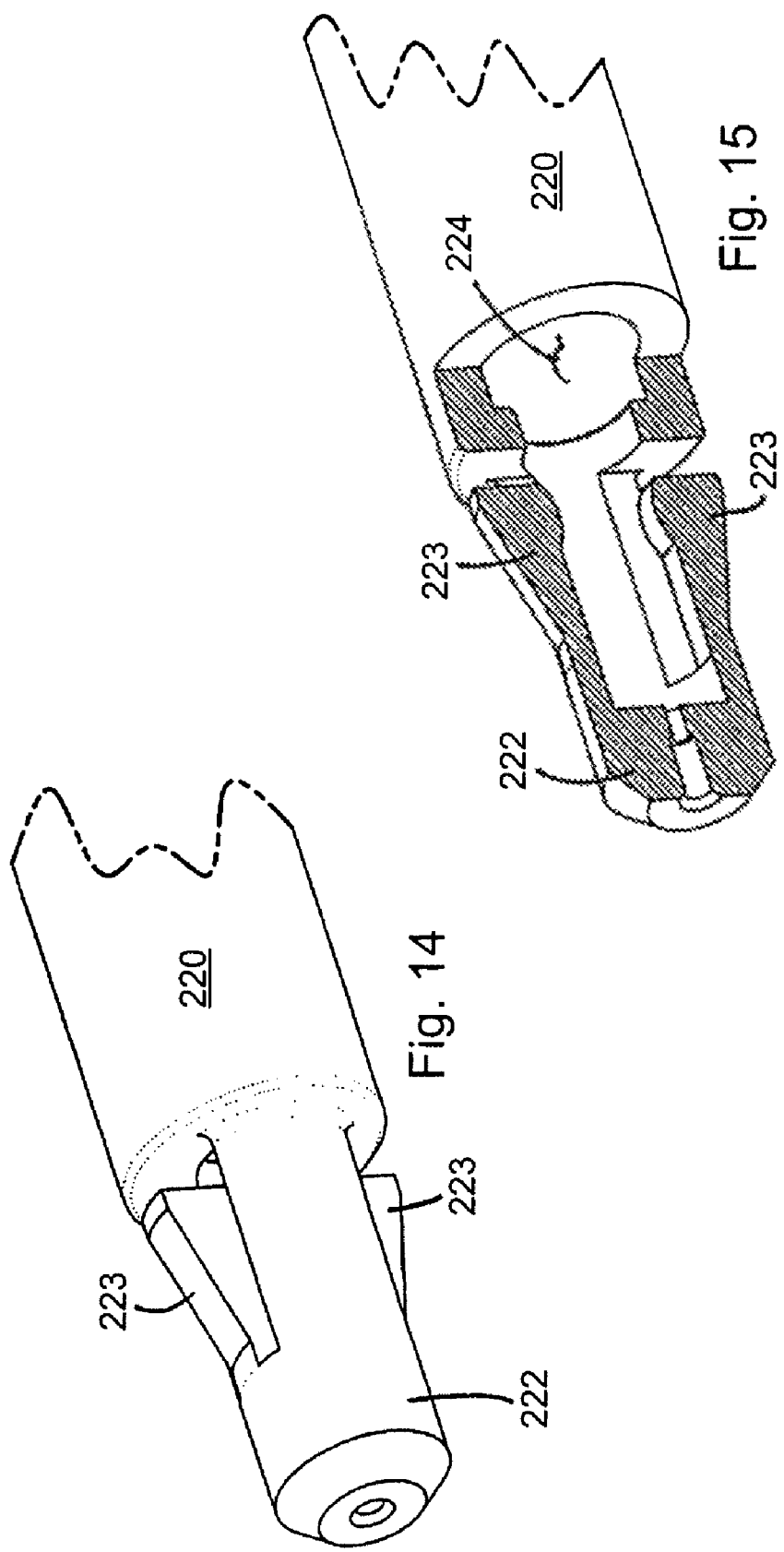

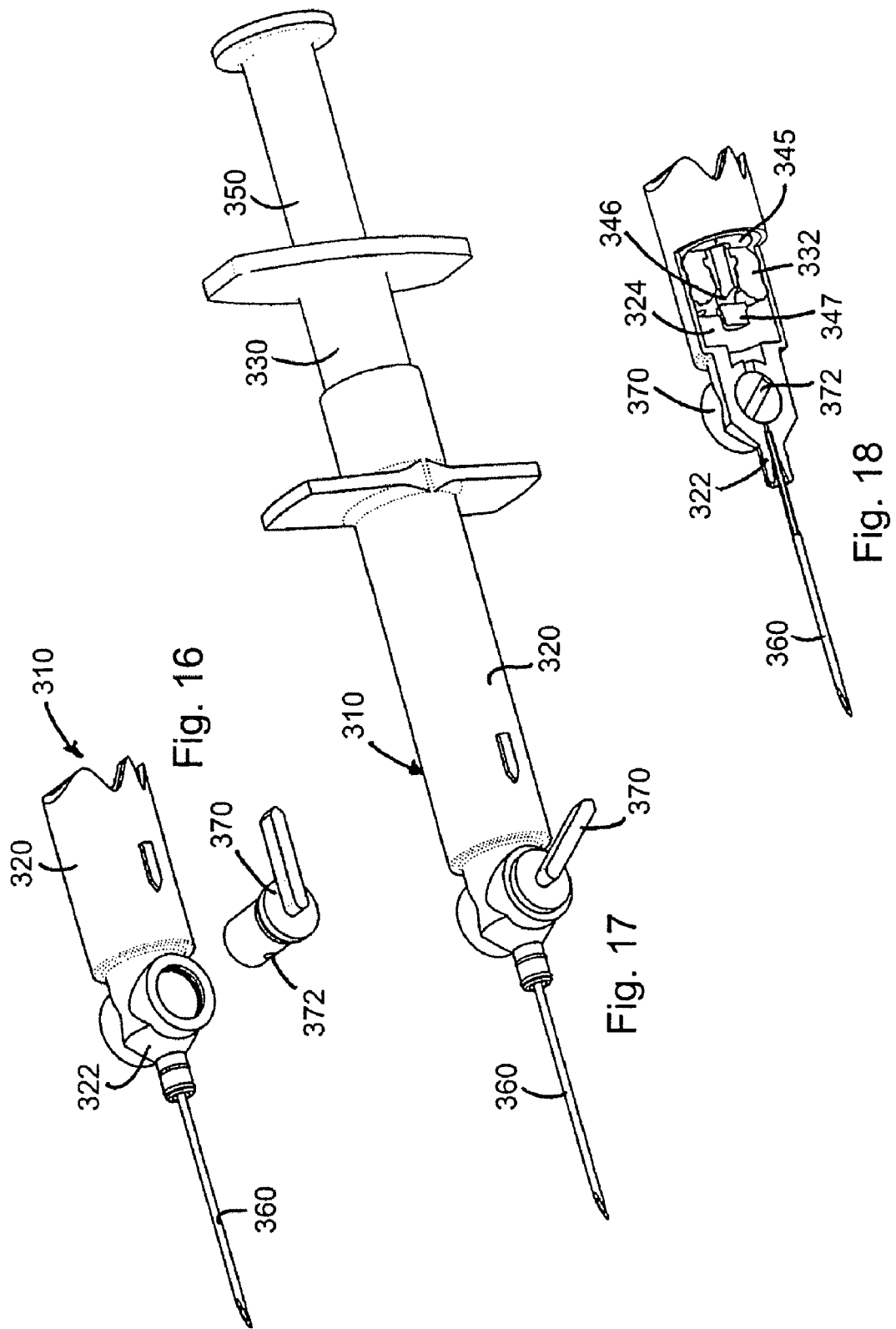

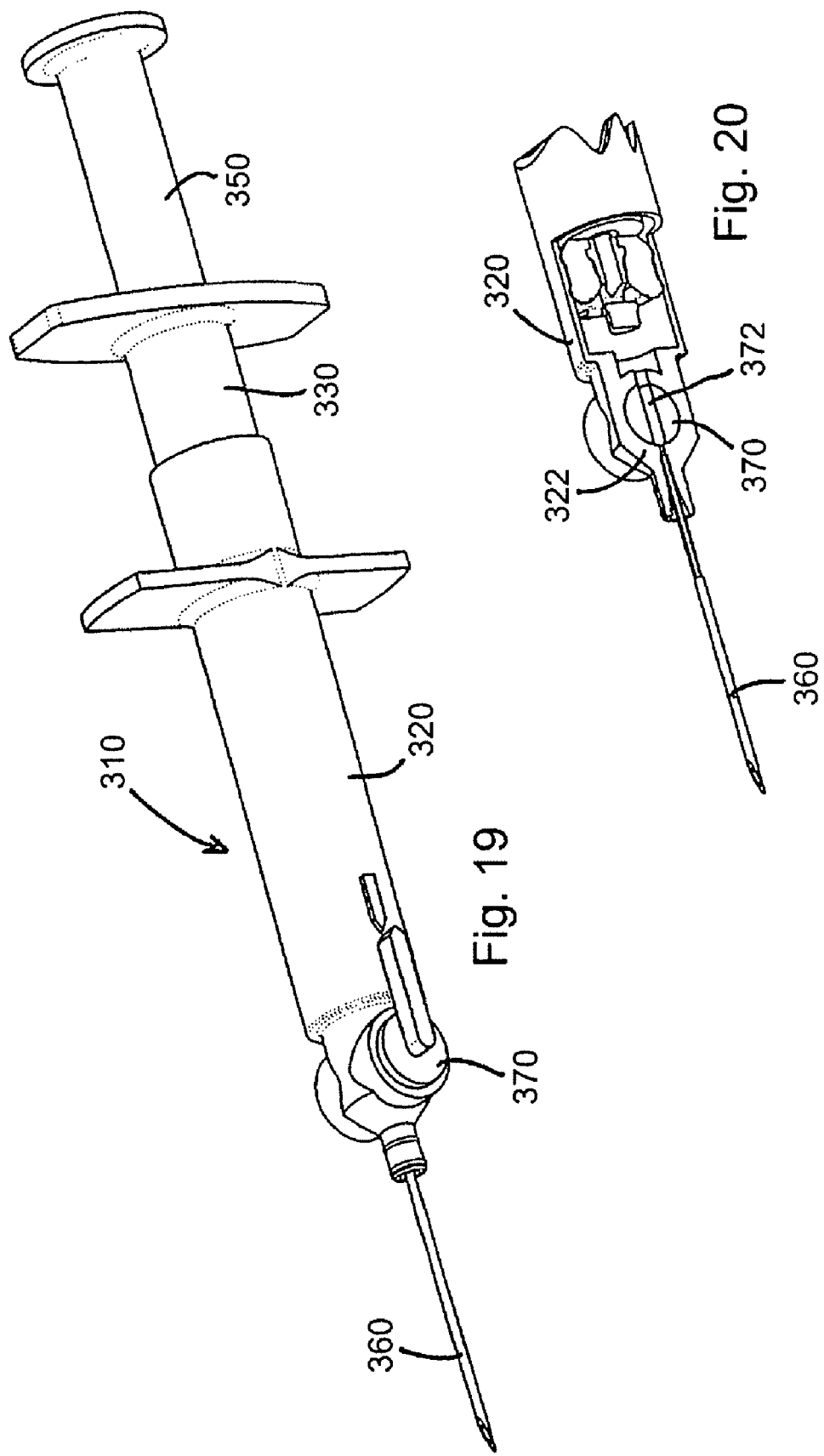

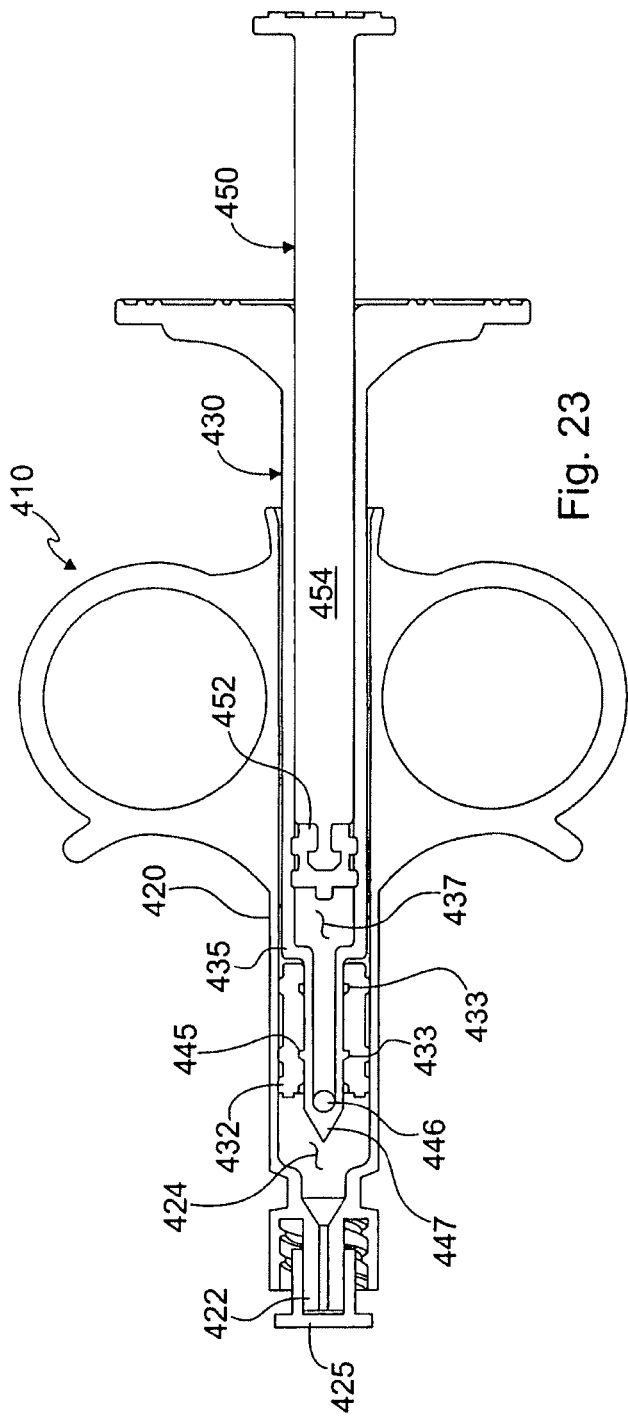
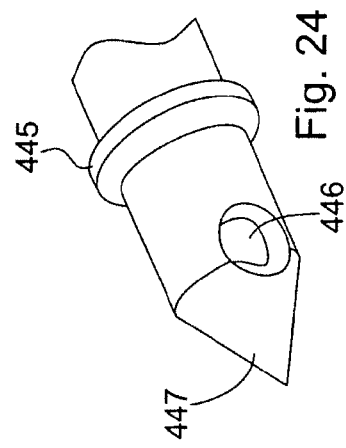
Fig. 23
Fig. 24

DUAL CHAMBER MIXING SYRINGE AND METHOD FOR USE

RELATED APPLICATIONS

This application is a continuation of prior U.S. patent application Ser. No. 10/972,985, filed on Oct. 25, 2004, which claims priority to U.S. Provisional Patent Application No. 60/514,045, filed on Oct. 24, 2003. The entire contents of each of the foregoing applications are hereby incorporated by reference herein.

FIELD OF THE INVENTION

The present invention relates to devices for mixing two components to form a mixture. More specifically, the present invention relates to a syringe having two chambers for receiving two constituents that are to be mixed, and the method for using such a device.

BACKGROUND OF THE INVENTION

Many drugs are stored in separate components that are mixed before use. Typically, the separate components include a powder and a liquid diluent. By storing the components separately, shelf life of the drug is increased.

With many of these drugs, the separate components are stored in a syringe and mixed within the syringe prior to use. The components are stored in separate chambers in the syringe prior to use. To prepare the medicine, the separate components are combined into a single chamber in the syringe, shaken and then the solution is ready for injection into a patient.

Although such a system works well for mixtures that are highly soluble, they are ineffective for less soluble mixtures. Specifically, the known systems combine the two components of a medicine into a single chamber and the mixture is then shaken to dissolve the components into solution. However, certain components cannot be adequately mixed by simply combining and shaking the two elements together.

SUMMARY OF THE INVENTION

In light of the foregoing shortcomings of the prior art and in order to provide an improved syringe, the present invention provides an improved syringe that is operable to mix separate components to prepare a medicinal fluid for use. The syringe is particularly suited to mix drugs having low viscosity and/or low solubility.

More specifically, the present invention provides a mixing syringe having a housing that includes a first fluid chamber for containing a first component of a medicine. Within the housing is a first plunger having a second fluid chamber for containing a second component of the medicine. Within the first plunger is a second plunger. A seal separates the first and second components, to prevent the components from becoming mixed during storage. Preferably, the syringe also includes a needle and a valve for preventing the discharge of the medicine through the needle while the components are being mixed.

Another aspect of the invention provides a method for mixing a medicine using a dual chamber syringe having a housing, a first plunger and a second plunger. A first component of the medicine is stored in a fluid chamber within the housing and a second component of the medicine is stored in a second chamber within the housing. Preferably, the second chamber is within the first plunger. A seal separates the two components during storage.

The method includes opening the separation seal to permit fluid flow between the first and second chambers to allow the two components to mix. The first plunger is displaced to drive the first components of the medicine into the second chamber. The second plunger is then displaced to drive the first and second components into the first chamber. The first and second plungers are then repeatedly displaced in an alternating fashion to drive the combined first and second components back and forth between the first and second chambers to mix the two components. After the components are mixed, either the first or second plunger is displaced forwardly to eject the mixture from the syringe.

Another aspect of the invention provides a syringe having two fluid chambers containing two medicinal components and a seal separating the components from one another. A needle is attached to the syringe housing, and a valve controls the flow of fluid from the housing through the needle.

BRIEF DESCRIPTION OF THE DRAWINGS

The foregoing summary and the following detailed description of the preferred embodiments of the present invention will be best understood when read in conjunction with the appended drawings, in which:

FIG. 1 is a dual chamber mixing syringe manifesting aspects of the present invention, shown in the syringe prior to use;

FIG. 2 is the syringe of FIG. 1, illustrating the syringe after a seal has been pierced;

FIG. 3 is the syringe of FIG. 1, illustrating the syringe after a first medicinal component has been transferred from a first fluid chamber to a second fluid chamber;

FIG. 4 is the syringe of FIG. 1, illustrating the syringe after the medicinal fluid has been transferred from the second fluid chamber back into the first fluid chamber;

FIG. 5 is the syringe of FIG. 4, illustrating the syringe with an applicator attached;

FIG. 6 is the syringe of FIG. 5, illustrating the syringe after the medicine is expelled from the syringe;

FIG. 7 is a side view partially in section of an alternative mixing syringe, illustrating the syringe prior to use;

FIG. 8 is a side view partially in section of the syringe of FIG. 7, illustrating the syringe after a valve has been opened;

FIG. 10 is an enlarged fragmentary perspective view of a valve element of the syringe;

FIG. 11 is an enlarged fragmentary cross-sectional view of the valve element of FIG. 10;

FIG. 12 is a fragmentary side view partially in section of a second alternative mixing syringe;

FIG. 13 is a fragmentary side view partially in section of the syringe of FIG. 12 with a needle cover removed;

FIG. 14 is a fragmentary perspective view of the forward end of the syringe illustrated in FIG. 12;

FIG. 15 is a fragmentary perspective view partially in section of the forward end of the syringe illustrated in FIG. 14;

FIG. 16 is a fragmentary partially exploded view of a third alternative mixing syringe;

FIG. 17 is a perspective view of the syringe illustrated in FIG. 16;

FIG. 18 is a fragmentary perspective view partially in section of the syringe illustrated in FIG. 17;

FIG. 19 is a perspective view of the syringe of FIG. 16, showing the syringe with a valve in an opened position;

FIG. 20 is a fragmentary perspective view partially in section of the syringe of FIG. 19;

FIG. 23 is a side cross-sectional view of the syringe illustrated in FIG. 22, illustrating the syringe after a seal has been pierced; and FIG. 24 is an enlarged fragmentary view of a portion of a plunger of the syringe illustrated in FIG. 22.

DETAILED DESCRIPTION OF THE INVENTION

Figure 9:
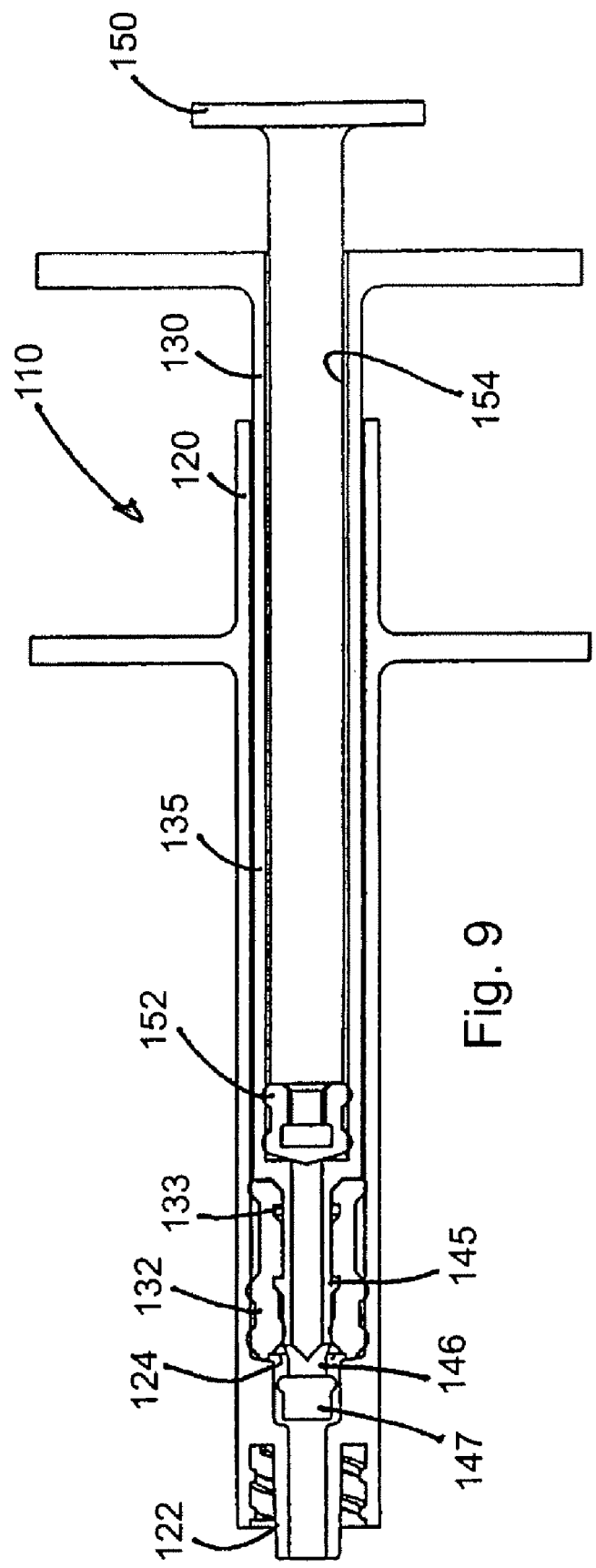
FIG. 9 is a cross sectional view of the syringe of FIG. 7, illustrating the syringe after medicine has been expelled from the syringe.
Figure 21:
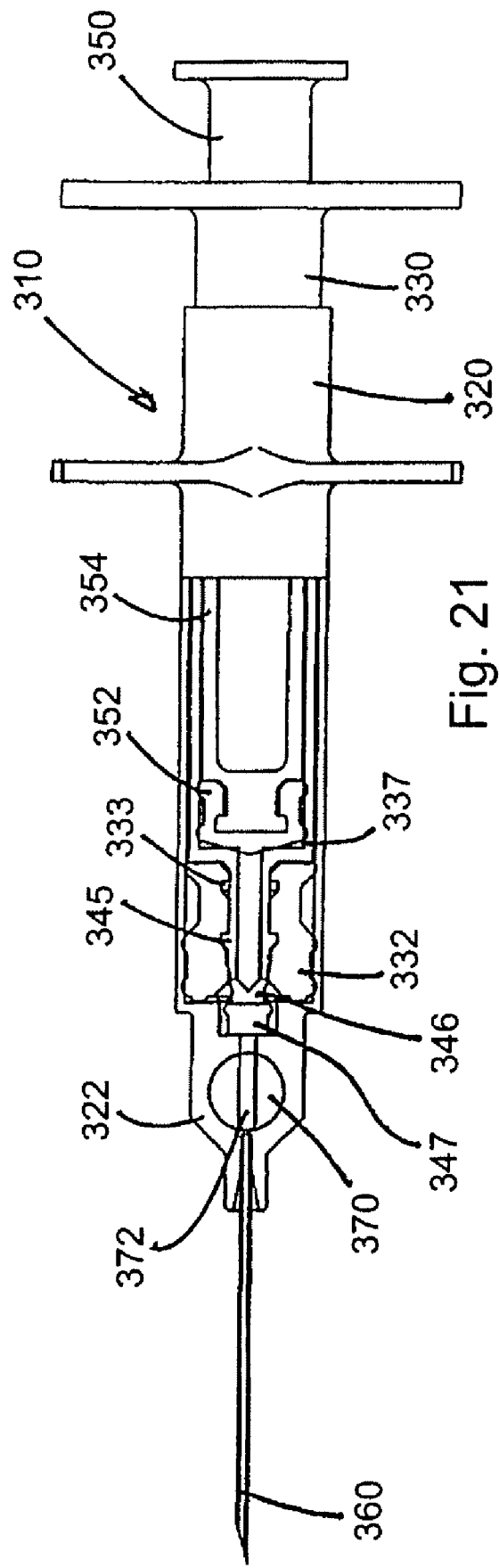
FIG. 21 is a side view partially in section of the syringe of FIG. 19.

Referring now to the figures generally, and to FIGS. 1-6 specifically, wherein like elements are numbered alike, a mixing syringe is designated generally 10. The syringe 10 is a dual chamber syringe that houses two components of a medicine and maintains the elements separately during storage. Prior to use, the elements are combined and mixed together within the syringe. Particularly, preferably the two components are mixed by repeatedly transferring the two components back and forth between two fluid chambers 24, 37 within the syringe 10. After the medicine is thoroughly mixed, the medicine is expelled from the syringe.

More specifically, the syringe 10 includes a hollow housing 20, a hollow outer plunger 30 disposed within the housing and an inner plunger 50 disposed within the outer plunger. A seal 25 on the end of the housing seals the housing closed. Preferably, a first medicinal component is stored within the housing 20 and a second component is stored within the outer plunger 30.

To mix the components, the first component is transferred into the outer plunger 30 by pushing the outer plunger forwardly. The two components are then transferred into the housing 20 by pushing the inner plunger 50 forwardly. To thoroughly mix the components together, the components are repeatedly transferred back and forth between the housing 20 and the chamber within the outer plunger 30 by alternatively pushing forward the outer plunger and the inner plunger. After the two components are thoroughly mixed, the seal 25 is removed and the medicine is expelled from the syringe by pushing forward one of the plungers.

Referring now to FIG. 1, the details of the syringe will now be described in greater detail. The outer housing 20 is configured similar to a typical syringe barrel. The rearward end of the housing is generally opened for receiving the outer barrel 30. The forward end of the housing is generally closed having a reduced diameter opening forming a discharge opening. Preferably, the forward end and the discharge opening forms a nozzle 22, such as a Luer lock fitting. The seal 25 is configured to cooperate with the nozzle to seal the forward opening of the housing 20. More specifically, preferably the seal comprises external threads that cooperate with the Luer lock threads so that the seal threadedly engages the housing.

Adjacent the rearward open end of the housing are a pair of opposing flanges 27 that project outwardly from the housing. The flanges form finger gripping elements for the operator to grasp during use. The interior of the housing forms a fluid chamber 24 and preferably the first medicinal component is stored in the fluid chamber in the housing as discussed further below.

The outer plunger 30 is configured to slide within the interior of the housing 20, similar to a plunger in a standard syringe. However, the outer plunger is hollow to receive the second medicinal component and the inner plunger 50 as discussed further below.

The outer plunger 30 comprises an elongated hollow plunger rod 35 and a piston 32 attached to the forward end of the plunger rod. The rearward end of the outer plunger 30 is generally opened for receiving the inner plunger 50. The forward end of outer plunger is generally closed, having a reduced diameter opening forming a fluid path for transferring the medicinal components between the housing and the interior of the outer plunger, as discussed further below.

Referring still to FIG. 1, the forward end of the outer plunger 30 preferably forms a tip that cooperates with the piston 32 to connect the piston to the outer plunger. Specifically, preferably the tip of the outer plunger rod 35 forms a barbed connector 45. In addition, preferably the outer plunger rod includes a piercing element 41 for piercing the seal that separates the two medicinal components. The piercing element may be formed in a variety of configurations. For instance, the piercing element may be a sharpened tip formed on the forward end of the tip of the outer plunger. However, preferably the piercing element 41 is a needle bonded to the tip of the outer plunger.

The piston 32 is an elastomeric element that forms a fluid-tight seal with the interior wall of the housing. The piston 32 has a bore forming a fluid path through the piston. A pierceable wall or septum 34 is formed in the piston to seal the fluid path through the piston. When the outer plunger is pushed further into the piston, the sharpened end of the needle 41 pierces the septum 34 and extends into a recess formed in the forward end of the piston 32. The recess in the forward end of the piston opens to the interior of the housing 20 so that when the needle 41 projects into the forward recess, the needle is in fluid communication with the interior of the housing, allowing medication to flow between the housing and the interior of the outer plunger.

At least one, and preferably two recesses 33 in piston 32 matingly engage the barb 45 of the outer plunger 30. Specifically, the piston 32 preferably includes two radially relieved portions or recesses 33a, 33b that mate with the head of the barb 45. The first radial recess 33a is formed in the piston 32 toward the rearward end of the piston, and the second radial recess 33b is formed in the interior of the piston adjacent to the septum 34. As shown in FIG. 1, prior to use, the plunger rod 35 is connected to the piston 32 so that the head of the barb 45 engages the first radial recess 33a in the piston. In this position, the needle 41 does not pierce the septum 34 of the piston 32. To prepare the device 10 for use, the medical professional displaces the outer plunger 30 forwardly relative to the piston 32, thereby displacing the head of the barb 45 into engagement with the second radial recess 33b, as shown in FIG. 2. At the same time, the needle 41 pierces the septum 34, so that the needle 41 is in fluid communication with the medicinal component in the housing 20.

The connection between the outer plunger 30 and the piston 32 is preferably a one-way engagement. In other words, when the piston 32 is mounted on the outer plunger 30, the plunger can be displaced forwardly relative to the piston, but the outer plunger can not be displaced rearwardly relative to the piston. In this way, the outer plunger cannot be readily removed from the piston 32, such that the outer plunger is substantially permanently attached to the piston.

The one-way connection is provided by a one-way sliding engagement between the barb 45 and the radial recesses 33a, 33b in piston 32. The barb 45 has forward-facing tapered edges that mate with tapered faces in the radial recesses 33a, 33b. The barb 45 also has sharp or square forward facing edges that mate with square edges in the radial recesses 33a, 33b. The tapered edges on the barb 45 and radial recesses 33a, 33b are tapered in the forward direction, permitting forward sliding displacement of the outer plunger 30 relative to the piston 32. The square edges on the barb 45 and in the recesses 33a, 33b operate as stops that impede forward displacement of the outer plunger 30 relative to the piston 32.

Adjacent the rearward open end of the outer plunger 30 are a pair of opposing flanges 39 that project outwardly from the outer plunger. The flanges form finger gripping elements for the operator to grasp during use. The interior of the outer plunger 30 is hollow, forming a fluid chamber 37 and preferably the second medicinal components is stored in the fluid chamber in the outer plunger as discussed further below.

The inner plunger 30 comprises an elongated hollow plunger rod 54 and a piston 52 attached to the forward end of the plunger rod. The inner plunger 50 is configured to slide within the interior chamber 37 of the outer plunger 30. More specifically, the piston 52 forms a fluid-tight seal with the interior wall of the fluid chamber 37 in the outer plunger 30. In this way, the inner plunger is operable to slide within the outer plunger to expel fluid from within the outer plunger.

Method of Use

Referring now to FIGS. 1-6, the operation of the syringe 10 will now be described in detail. In FIG. 1 the syringe is shown prior to use. More specifically, the configuration in FIG. 1 is referred to as an "as-shipped" configuration, and is the configuration in which the syringe is stored prior to use. In this "as-shipped" configuration, the first medicinal component is preferably in the fluid chamber 24 in the housing and the second medicinal component is preferably in the fluid chamber 37 in the outer barrel.

The two components of the medicine may both be fluids, however, one components can be a liquid diluent and the other element may be a powder. In the present instance, preferably, a liquid component is preferably stored in the housing 20 and a powder component is preferably stored in the outer plunger 30. In the "as-shipped" configuration in FIG. 1, the powder and liquid components are maintained separately by the septum 34 in piston 32, that has not been pierced by the needle 41.

Referring now to FIG. 2, to prepare the syringe for use, the outer plunger 30 is displaced forwardly. The operator displaces the outer plunger by grasping the finger grips 27 on the housing and the finger grips 39 on the outer plunger and squeezing the two together to push the outer barrel forward. Since fluid is disposed in the housing, and the fluid is incompressible, the fluid maintains the piston in place while the plunger rod 35 is displaced forwardly. In this way, the barbed connector 45 on the end of the piston rod 35 is displaced forwardly disengaging the first recess 33a in the piston 32 and engaging the second recess 33b. As the plunger rod 35 is displaced forwardly relative to the piston 32, the needle 41 pierces the septum 34. By piercing the septum 34, the fluid path through the piston 32 and the tip of the plunger rod 35 is opened, so that the fluid chamber 24 in the housing and the fluid chamber in the outer plunger are in fluid communication.

Referring now to FIG. 3, after the septum 34 is pierced as shown in FIG. 2, the two medicinal components are combined together. More specifically, preferably, the fluid component in the housing 20 is transferred to the fluid chamber 37 within the outer plunger 30. The fluid is transferred by continuing to push on the outer barrel by grasping the finger grips 27, 39 on the housing and the outer plunger and squeezing them together. Since the seal 25 seals the forward end of the housing, when the outer plunger 30 moves forward the fluid has no where to go but into the fluid chamber within the outer plunger. More specifically, pushing the outer plunger forwardly causes the fluid to flow out of the fluid chamber 24 in the housing through the piston 32, the needle 41 and the tip of the plunger rod 35, and into the fluid chamber in the outer plunger 30. As the fluid enters the outer plunger 30, the fluid pressure created by the fluid transfer displaces inner plunger 50 rearwardly to provide a larger area in the outer plunger to accommodate the fluid. By pushing the outer plunger 30 forwardly until the piston 32 abuts the forward end of the housing, substantially all of the fluid is transferred out of the housing fluid chamber 24 and into the outer plunger fluid chamber 37.

As described above, the transfer of the fluid from the housing 20 to the outer plunger 30 is aided by the fact that the forward end of the housing is sealed by seal 25. Accordingly, it is desirable to provide a connection between the seal 25 and the nozzle 22 that can withstand the high fluid pressures created during the transfer, and maintain the fluid seal. Although a frictional engagement between the nozzle and the seal may be sufficient in certain instances, preferably the nozzle and seal have a stronger mechanical engagement such as a threaded engagement.

Referring to FIGS. 3 and 4, once the components of the medicine are combined in a single chamber, the components are to be mixed. In certain applications, the components can be sufficiently mixed by simply shaking the syringe after the components are combined. However, with certain low solubility mixtures and/or high viscosity fluids, more rigorous mixing is necessary to properly prepare the medicine for use.

Accordingly, preferably the mixture is transferred back and forth between the outer plunger 30 and the housing 20. The mixture is transferred to the housing 20 by displacing the inner plunger 50 forwardly, as shown in FIG. 4. More specifically, the operator grasps the finger grips 39 on the outer barrel and a push pad on the end of the inner plunger 50 and squeezes them together. This action displaces the inner plunger 50 forwardly within the fluid chamber 37 in the outer plunger 30, thereby displacing the mixture forwardly through the fluid path in the tip of the plunger rod 35, the needle 41 and the piston 32. The fluid pressure created from the transfer of the mixture into the housing 20 drives the outer plunger 30 rearwardly relative to the housing, so that the fluid chamber 24 in the housing expands to accommodate the volume of the mixture along with any air that was in the outer plunger.

To continue mixing the mixture, the mixture is transferred back into the outer plunger 30 by pushing the outer plunger forward, as described above. Again, the mixture can be further mixed by transferring the mixture back into the housing by pushing forward the inner rod. In this way, the mixture can be thoroughly mixed by repeatedly transferring the mixture between the chamber 24 in the housing and the chamber 37 in the outer plunger. The repeated transfer is accomplished by alternatively pushing forward the outer plunger 30 and the inner plunger 50. The number of times that the mixture needs to be transferred to mix the medicine sufficiently depends upon the characteristics of the two components. In some instances it may only require a few transfers of the components. In other instances it may require upwards of 100 or more transfers to mix the components sufficiently.

Referring now to FIG. 5, once the mixture is thoroughly mixed, the seal 25 is removed from the housing and a dispenser tip is connected to the nozzle 22. The mixture can be expelled from the syringe directly from the outer plunger 30 by displacing the inner plunger 50 forwardly. However, preferably, before the seal 25 is removed, the mixture is transferred into the chamber in the housing.

The dispenser tip 60 can be any of a variety of tips depending upon the procedure employed for using the medicine. As shown in FIG. 5, the dispenser tip can be a tapered nozzle shaped tip. In other applications the dispenser tip may be a needle for injecting the mixture into a patient.

Referring now to FIG. 6, after the dispenser tip is attached, the mixture is expelled by pushing the outer plunger 30 forwardly within the housing 20. The outer plunger 30 is pushed forward until the piston 32 abuts the forward wall of the housing to thereby expel all of the mixture from the syringe 10.

Referring now to FIGS. 7-11 an alternative embodiment of a syringe is designated generally 110. The syringe 110 in this alternative embodiment operates substantially similar to the syringe 10 described above. Referring to the previously described syringe, the syringe includes a seal to separate the two components during storage. In the previously described syringe 10 the seal is provided by a pierceable wall or septum 34. However, various alternative sealing elements can be utilized to separate the two components during storage. The alternative embodiment shown in FIGS. 7-11 describes a seal that is different from the seal 34 in the first embodiment. All of the remaining elements in the alternative embodiment are preferably substantially similar to the elements illustrated in FIGS. 1-6 and described above.

The syringe 110 includes a hollow housing 120 having a nozzle 122, a fluid chamber 124, a seal 125 and finger grips 127. Each of these elements is substantially similar to the housing 20, nozzle 22, fluid chamber 24, seal 25 and finger grips described previously for the first embodiment, except as otherwise discussed below. In addition, the syringe 110 includes an inner plunger 150 that has an elongated plunger rod 154 and a piston 152, that are substantially similar to the plunger 50, plunger rod 54 and piston 52 described previously for the first embodiment, and forming a fluid-tight seal with the interior of the outer plunger 130.

The outer plunger 130 includes a plunger rod 135 and a piston 132 that forms a fluid-tight seal with the inner wall of the fluid chamber 124 in the housing 120. The outer plunger 130 is hollow, forming a fluid chamber 137 for receiving a component of the medicine.

The piston 132 is attached to the plunger rod 135 using a barbed connector 145 similar to the syringe 10 described previously. More specifically, as in the previous embodiment, preferably the piston 132 includes a pair of recess 133 that are configured to cooperate with the barbed connector in a manner similar to the connection described above in detail in connection with the first syringe 10. Accordingly, the description of the details of the recesses 133 and the barbed connector 145 and the details of operation of these elements are similar to those described above in connection with the recess 33a, 33b and the barbed connector 45 of the first syringe 10.

The piston 132 and the plunger rod 135 are configured differently from the previously described piston 32 and plunger rod 35 to provide a different seal between the housing fluid chamber 124 and the outer plunger fluid chamber 137. Specifically, the end of the plunger rod 135 forms a tip 147 having an circumferential rib that seats with the bore in the piston 132 to form a fluid-tight seal. A side port 146 in the end of the plunger rod 135 spaced rearwardly from the tip 147 provides a fluid passageway around the tip.

Referring to FIGS. 7, 10-11, in the "as-shipped" configuration, the barb 145 is in the first recess 133. In this position, the tip 147 is disposed within the piston 132 and the interior bore of the piston forms a fluid-tight seal with the tip to seal the fluid path through the piston and the end of the plunger rod 135. Referring to FIGS. 8, 10-11, by pushing forward on the outer plunger, the barb is displaced into engagement with the second recess 133 and the tip is displaced forwardly from the piston 132 so that the side port 146 is no longer sealed by the piston. In this way, the piston 132 and the end of the plunger rod 135 operate similarly to a sliding valve. In the open position illustrated in FIG. 8, a substantially unobstructed fluid path is provided between the housing fluid chamber 124 and the outer plunger fluid chamber 137. The fluid flows from the housing 120 through the side port 146 through the conduit in the barbed connector 135 and into the outer plunger.

Referring now to FIG. 9, in order to limit dead space in the syringe 110, preferably the forward end of the fluid chamber 124 in the housing is configured to cooperate with the end of the outer plunger 130. More specifically, as can be seen in FIGS. 8 and 9, the tip 147 of the outer plunger extends forwardly from the piston 132. Accordingly, preferably the housing fluid chamber 124 has a constricted forward portion that closely corresponds to the diameter of the tip 147. In this way, there is less room for residual medicine to remain in the housing after the piston engages the forward end of the housing 120.

Referring now to FIGS. 12-15 a second alternative syringe is designated generally 210. The syringe 210 illustrated in FIGS. 12-15 is similar to the syringe 110 illustrated in FIGS. 7-11 and described above. However, the syringe 210 includes a needle 260 attached to the housing, and a seal or valve that is operable to prevent the discharge of medicine through the needle while the components are mixed within the syringe in a manner similar to the method described previously.

The syringe 210 includes a housing 220 having a fluid chamber 224. An outer plunger 230 having a piston 232, plunger rod 235, fluid chamber 237, barbed connector 245, side port 246 and tip 247 that are substantially similar to the piston 132, plunger rod 135, fluid chamber 137, barbed connector 145, side port 146 and tip 147 described above in connection with the previous embodiment 110.

The syringe further includes an inner plunger having an elongated piston rod and piston seal that are substantially similar to the piston rod and piston of the previous embodiments 52, 54, 152, 154. In addition, as in previous embodiments, the inner piston forms a fluid-tight seal with the fluid chamber in the outer plunger 230.

Referring to FIGS. 14-15, the details of the tip of the housing will be described in greater detail. The tip 222 of the housing 220 includes a pair of molded cut-outs so that two radially displaceable arms 223 are formed in the wall of the tip of the housing. The arms are molded so that they are biased outwardly so that the arms project outward from the external surface of the tip 222.

A flexible conduit 228 is disposed within the tip 222 of the housing. The flexible conduit 228 is formed of an elastomeric material so that the walls of the conduit are resiliently radially deformable. Accordingly, when the arms 223 are displaced radially inwardly the ends of the arms pinch the flexible conduit 228 sealing off the fluid pathway through the flexible conduit.

As shown in FIGS. 12-13, the forward end of the tip forms a reduced diameter bore. The needle is fixedly attached to the tip within the reduced diameter bore.

Referring now to FIG. 12, the syringe includes a needle shield 265 that serves two functions: the shield encloses the needle to prevent inadvertent contact with the needle prior to use; and the shield squeezes the arms 223 inwardly to seal off the fluid pathway through the flexible conduit 228. More specifically, the needle shield has an open rearward end having an internal bore configured similarly to the exterior surface of the tip of the housing 222. In this way, when the needle shield 265 is attached to the tip 222 of the housing, the needle shield compresses the tip, displacing the arms 223 inwardly so that the arms pinch closed the flexible conduit. The seal provided by the pinched conduit is sufficient to withstand the fluid pressure generated during the transfer of fluid between the fluid chamber 224 in the forward end of the housing and the fluid chamber 237 in the outer plunger 237 during the mixing process, which is described previously in connection with the first syringe 10.

Referring to FIG. 13, after the medicine is mixed in the syringe 210, the needle shield 265 is removed. The arms 223 resiliently rebound and displace radially outwardly thereby unclamping the flexible conduit 228. In this way, removing the needle shield opens the fluid path through the flexible conduit so that the medicine in the housing can be expelled through the needle to provide an injection.

Referring now to FIGS. 16-21 a third alternative syringe 310 is illustrated. The syringe 310 illustrated in FIGS. 12-15 is similar to the syringe 210 illustrated in FIGS. 12-15 and described above. However, the syringe 310 includes a alternate valve or seal sealing the housing to prevent the discharge of medicine through the needle while the components are mixed within the syringe in a manner similar to the method described previously.

The syringe 310 includes a housing 320 having a fluid chamber 324. An outer plunger 330 having a piston 332, plunger rod 335, fluid chamber 337, barbed connector 345, side port 346 and tip 347 that are substantially similar to the piston 132, plunger rod 135, fluid chamber 137, barbed connector 145, side port 146 and tip 147 described above in connection with previous embodiment 110.

The syringe 310 further includes an inner plunger 350 having an elongated piston rod 354 and piston seal 352 that are substantially similar to the piston rod and piston of the previous embodiments 52, 54, 152, 154. In addition, as in previous embodiments, the inner piston forms a fluid-tight seal with the fluid chamber in the outer plunger 330.

Referring to FIGS. 16-18, the details of the tip of the housing 220 will be described in greater detail. The tip 322 of the housing is configured to accommodate a rotary valve 370 that controls the flow of fluid from the housing 320 through the needle 360. Specifically, referring to FIGS. 16 and 18, the tip 322 includes a side bore for receiving the valve 370, and a fluid passage way that cooperates with the valve as discussed further below.

The valve 370 is a cylindrical element having a fluid passageway 372. When the fluid passageway 372 is aligned with the fluid passageway through the tip (see FIG. 20), the valve is open and fluid can flow through the needle. When the fluid passageway 372 through the valve 370 is mis-aligned with the fluid passageway in the tip 322 (see FIG. 18), the valve is closed and is prevents the flow of fluid through the needle. Accordingly, the valve 370 is operable between an opened position and a closed position to control the flow of fluid through the needle. As in the previous embodiment, the valve 370 is configured to withstand the fluid pressure created during the transfer of the components in the mixing process. As shown in FIGS. 17 and 19, the valve includes an external lever for rotating the valve between the opened and closed positions.

Configured in this way, the syringe 310 is operable to mix two components as described above while the needle is attached, while also preventing the medicine from being discharged from the syringe during the mixing process. After the medicine is mixed, the valve is rotated into the opened position and the medicine can be expelled by pushing the outer plunger forwardly.

Figure 22:
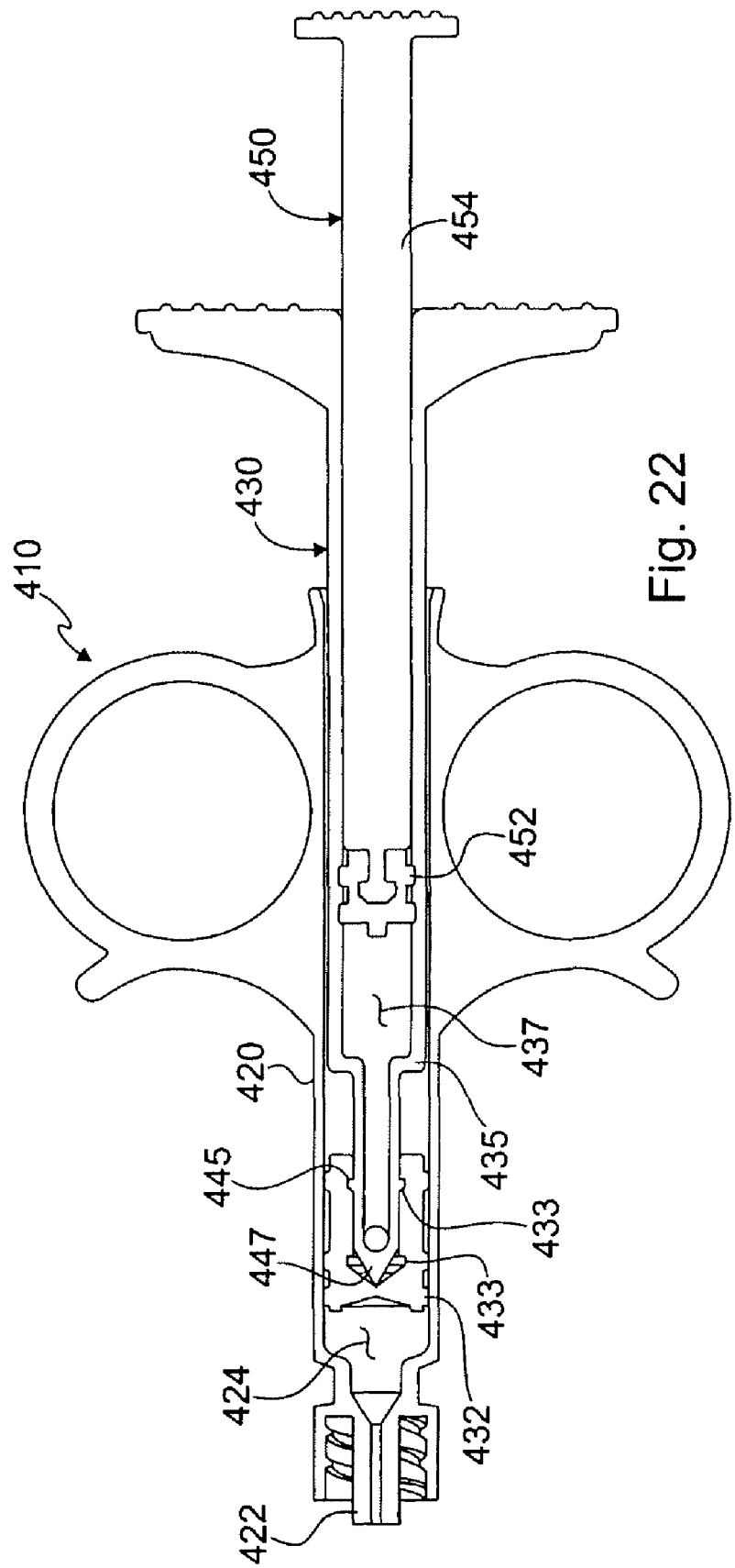
FIG. 22 is a side cross-sectional view of a fourth alternative mixing syringe.

Referring now to FIGS. 22-24 a third alternative embodiment of a syringe is designated generally 410. The syringe 410 in this alternative embodiment operates substantially similar to the syringe 10 described above. Referring to the previously described syringe, the syringe includes a seal to separate the two components during storage. In the previously described syringe 10 the seal is provided by a pierceable wall or septum 34. The outer plunger 30 has a piercing element 41 in the form of a needle that is operable to pierce the seal 34. In the present embodiment 410, the outer plunger 430 includes a piercing element 441 in the form of a spear that is operable to pierce the seal. The remaining elements in the alternative embodiment are preferably substantially similar to the elements illustrated in FIGS. 1-6 and described above.

The syringe 410 includes a hollow housing 420 having a nozzle 422, a fluid chamber 424, and a seal 425. Each of these elements is similar to the housing 20, nozzle 22, fluid chamber 24, and seal 25 described previously for the first embodiment, except as otherwise discussed below. In addition, the syringe 410 includes an inner plunger 450 that has an elongated plunger rod 454 and a piston 452, that are substantially similar to the plunger 50, plunger rod 54 and piston 52 described previously for the first embodiment, and forming a fluid-tight seal with the interior of the outer plunger 430.

The outer plunger 430 includes a plunger rod 435 and a piston 432 that forms a fluid-tight seal with the inner wall of the fluid chamber 424 in the housing 420. The outer plunger 430 is hollow, forming a fluid chamber 437 for receiving a component of the medicine.

The piston 432 is attached to the plunger rod 435 using a barbed connector 445 similar to the syringe 10 described previously. More specifically, as in the previous embodiment, preferably the piston 432 includes a pair of recess 433 that are configured to cooperate with the barbed connector in a manner similar to the connection described above in detail in connection with the first syringe 10. Accordingly, the description of the details of the recesses 433 and the barbed connector 445 and the details of operation of these elements are similar to those described above in connection with the recess 33a, 33b and the barbed connector 45 of the first syringe 10.

The piston 432 and the plunger rod 435 are configured differently from the previously described piston 32 and plunger rod 35 to provide a different piercing mechanism. Specifically, the end of the plunger rod 435 forms a conical tip 447 forming a point or spear. In the present embodiment, the tip 447 is integrally formed with the outer plunger rod 435 as a single molded part. A side port 446 in the end of the plunger rod 435 spaced rearwardly from the tip 447 provides a fluid passageway around the tip.

Referring to FIG. 22, in the "as-shipped" configuration, the barb 445 is in the first recess 433. In this position, the tip 447 is disposed within the piston 432 and the interior bore of the piston forms a fluid-tight seal with the tip to seal the fluid path through the piston and the end of the plunger rod 435. Referring to FIG. 23, by pushing forward on the outer plunger, the barb is displaced into engagement with the second recess 433, the tip 447 pierces the seal 434 and the tip 447 is displaced forwardly from the piston 432 so that the side port 446 is no longer sealed by the piston. In the open position illustrated in FIG. 23, a substantially unobstructed fluid path is provided between the housing fluid chamber 424 and the outer plunger fluid chamber 437. The fluid flows from the housing 420 through the side port 446 through the conduit in the barbed connector 435 and into the outer plunger.

Referring now to FIG. 23, in order to limit dead space in the syringe 410, preferably the forward end of the fluid chamber 424 in the housing is configured to cooperate with the end of the outer plunger 430. More specifically, as can be seen in FIG. 23, the tip 447 of the outer plunger extends forwardly from the piston 432. Accordingly, preferably the housing fluid chamber 424 has a constricted forward portion that closely corresponds to the diameter of the tip 447. In this way, there is less room for residual medicine to remain in the housing after the piston engages the forward end of the housing 420.

It will be recognized by those skilled in the art that changes or modifications may be made to the above-described embodiments without departing from the broad inventive concepts of the invention. For instance, the device has been described as operable to mix together two components of a medicinal fluid. The components may be a fluid and a dry powder. Alternatively, the two components may both be fluid. In certain applications, one or more of the materials may be a relatively highly viscous material. Furthermore, the present mixing syringe and the method of use are not limited to applications in which medicinal fluids are mixed. For instance, the syringe and its use are applicable to a wide range of applications for mixing two-part mixtures. For example, the syringe and method of use can be used mix two-part epoxy. It should therefore be understood that this invention is not limited to the particular embodiments described herein, but is intended to include all changes and modifications that are within the scope and spirit of the invention as set forth in the claims.

The invention claimed is:

1. A mixing syringe comprising:
 a needle;
 a housing defining a first chamber that includes a first component of a mixture therein, wherein the needle is attached to the housing, and wherein the housing comprises a valve configured to selectively seal a pathway between the first chamber and the needle;
 a first plunger configured to slide within the housing, wherein the first plunger defines a second chamber that includes a second component of the mixture therein;
 a plunger rod including a rib that forms a fluid tight seal in a closed state and a side port providing a fluid passageway in an open state, the first component separated from the second component in the closed state; and
 a second plunger configured to slide within the first plunger;
 wherein the first plunger is configured to transfer the first component from the first chamber to the second chamber when the fluid passageway is in the open state and the first plunger is displaced forwardly, wherein the second plunger is configured to transfer the second component from the second chamber to the first chamber when the fluid passageway is in the open state and the second plunger is displaced forwardly, and
 wherein the valve is configured to seal the pathway between the first chamber and the needle to permit mixing of the first component and the second component and to be opened to permit the mixed first and second components to pass through the pathway.

2. The syringe of claim 1, wherein the plunger rod is displaceable relative to the housing.

3. The syringe of claim 2, wherein the forward end of the housing defines a constricted portion for receiving a tip of the plunger rod.

4. The syringe of claim 1, wherein the valve comprises a valve element that is displaceable relative to a portion of the housing.

5. The syringe of claim 4, wherein the valve comprises a rotary valve.

6. The syringe of claim 1, wherein the plunger rod is connected to the first plunger so that the plunger rod is displaceable when the first plunger is displaced.

7. The syringe of claim 1, wherein the first plunger comprises a piston that is connected to the first plunger prior to use.

8. The syringe of claim 1, wherein the first plunger comprises a piston that defines the path between the first and second chambers.

9. The syringe of claim 1, wherein the plunger rod has a stem and a piston having a connector cooperable with the stem, and wherein the stem and the connector are operable to connect the piston to the plunger rod without unsealing the seal.

10. The syringe of claim 9, wherein the connector comprises a pocket cooperable with the stem.

11. The syringe of claim 1, wherein at least one of the first and second components comprises a fluid.

12. The syringe of claim 1, wherein one of the first and second components comprises a powder.

13. A mixing syringe comprising:
 a needle;
 a hollow housing attached to the needle, wherein the housing defines a first chamber that contains a first component of a medicine;
 a second chamber at least partially within the housing that contains a second component of the medicine;
 a first plunger configured to slide within the housing;
 a plunger rod including a rib that forms a fluid tight seal in a closed state and a side port providing a fluid passageway in an open state, the first component separated from the second component in the closed state; and
 a valve operable to prevent movement of one or more of the first and second components from the first chamber through the needle when in a first orientation and to allow movement of one or more of the first and second components from the first chamber through the needle when in a second orientation,
 wherein the first plunger is configured to move the first component from the first chamber to the second chamber when the fluid passageway is in the open state and when the first plunger is displaced toward a forward end of the housing, and
 wherein a second plunger is configured to move the second component from the second chamber to the first chamber when the fluid passageway is in the open state and when the second plunger is displaced toward the forward end of the housing.

14. The syringe of claim 13, wherein the plunger rod is displaceable relative to the housing.

15. The syringe of claim 14, wherein the forward end of the housing defines a constricted portion for receiving a tip of the valve element.

16. The syringe of claim 13, wherein the valve comprises a valve element that is displaceable relative to a portion of the housing.

17. The syringe of claim 16, wherein the valve comprises a rotary valve.

18. The syringe of claim 13, wherein the plunger rod is connected to the first plunger so that the plunger rod is displaceable when the first plunger is displaced.

19. The syringe of claim 13, wherein displacement of the first plunger is operable to move the plunger rod to open the fluid passageway to allow movement of one or more of the first and second components between the first chamber and the second chamber.

20. The syringe of claim 13, wherein the first plunger comprises a piston that is connected to the first plunger prior to use.

21. The syringe of claim 13, wherein the first plunger comprises a piston and a path through the piston, wherein the plunger rod seals the path through the piston.

22. The syringe of claim 13, wherein the plunger rod has a stem and a piston having a connector cooperable with the stem, wherein the stem and the connector are operable to connect the piston to the plunger rod without unsealing the seal.

* * * * *